United States Patent [19]

Goodenow et al.

[11] Patent Number: 5,385,888

[45] Date of Patent: Jan. 31, 1995

[54] CLASS I MHC MODULATION OR SURFACE RECEPTOR ACTIVITY

[75] Inventors: Robert S. Goodenow; Lennart Olsson, both of Orinda, Calif.

[73] Assignee: The Regents of the University of California, Oakland, Calif.

[21] Appl. No.: 57,184

[22] Filed: May 3, 1993

Related U.S. Application Data

[63] Continuation of Ser. No. 649,471, Feb. 1, 1991, abandoned, which is a continuation-in-part of Ser. No. 323,565, Mar. 14, 1989, abandoned, which is a continuation-in-part of Ser. No. 28,241, Mar. 20, 1987, abandoned.

[51] Int. Cl.$^6$ .................. A61K 37/02; C07K 7/06
[52] U.S. Cl. ............................ 514/12; 514/2; 514/8; 514/16; 530/300; 530/324; 530/328
[58] Field of Search ............ 424/88; 514/2, 8, 12–16; 530/324, 350, 395, 328

[56] References Cited

U.S. PATENT DOCUMENTS 5,073,540 12/1991 Olsson ........................ 514/3

OTHER PUBLICATIONS

Due, C., et al., P.N.A.S. (USA) 83:6007–6011 (Aug. 1986), "The major histocompatibility complex class I heavy chain as a structural subunit of the human cell membrane insulin receptor: implications for the range of biological functions of histocompatibility antigens".
Fehlmann, M., et al., P.N.A.S. (USA) 82:8634–8637 (Dec., 1985), "Molecular association between major histocompatibility complex class I antigens and insulin receptors in mouse liver membranes".
Gilman, A. G., et al., *The Pharmacological Basis of Therapeutics*, 8th edition, pp. 1468–1470 (1990).
Kittur, D., et al., P.N.A.S. (USA) 84:1351–1355 (Mar., 1987), "Insulin binding to human B lympoblasts is a function of HLA haplotype".
Lafuse, W., et al., Biochemistry 1:49–54 (1980), "Interaction of the mouse major histocompatibility complex, H-2, on liver adenylate cyclase activity and on glucagon binding to liver cell membranes".
Paul, W. F. (ed), *Fundamental Immunology*, 2d edition (1989), pp. 652–653.
Phillips, M., et al., P.N.A.S. (USA) 83:3474–3478 (May, 1986, "Class I histocompatibility antigens and insulin receptors: evidence for interactions".
*Robbins Pathological Basis of Disease* (R. S. Cotran, et al., eds.), 4th edition (1989), pp. 994–1001.
Ruoslahti, E., et al. in *Synthetic Peptides in Biology and Medicine*, pp. 191–197 (1985), Alitalo, et al (editors), Elsevier Science Publishers B. V. (Biomedical Division), the Netherlands.
Schreiber, A. B., et al., J. Cell Biol. 98:725–731 (Feb., 1984), "Interaction between major histocompatibility complex antigens and epidermal growth factor receptors on human cells".
Simonsen, M., et al., Ann. Immunology (Inst. Pasteur) 134D, pp. 85–92 (1983), "Possible roles of compound membrane receptors in the immune system".

*Primary Examiner*—Christine M. Nucker
*Assistant Examiner*—Thomas Cunningham
*Attorney, Agent, or Firm*—Bertram I. Rowland

[57] ABSTRACT

Methods and compositions are provided for regulating surface membrane receptor response by modulating the interaction between an MHC Class I antigen and the surface membrane receptor. Various techniques may be employed for enhancing or reducing the interaction between the Class I antigen and surface membrane receptor, e.g., enhancing production of the Class I antigen.

2 Claims, No Drawings

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp Thr Xaa Phe Val Arg Phe Asp Ser Asp Xaa Xaa

```
                   1               5                          10
```

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Phe  Val  Arg  Phe  Asp  Ser  Asp  Xaa  Xaa  Ser  Pro  Arg  Xaa
1                   5                        10
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Trp  Xaa  Glu  Gln  Xaa  Xaa  Gly  Pro  Glu  Tyr  Trp
1                   5                        10
```

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Trp  Xaa  Xaa  Xaa  Thr  Xaa  Xaa  Xaa  Lys  Xaa  Xaa  Xaa  Gln
1                   5                        10
```

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Trp  Xaa  Xaa  Xaa  Xaa  Xaa  Xaa  Xaa  Lys  Xaa  Xaa  Xaa  Xaa  Xaa  Xaa  Xaa
1                   5                        10                           15

Xaa  Xaa  Xaa  Xaa  Xaa  Xaa  Xaa  Xaa  Xaa  Xaa
               20                        25
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Glu Gln Xaa Xaa Arg Val Xaa Xaa Arg Xaa Xaa Xaa Arg Tyr Tyr
1               5                   10                  15
```

(2) INFORMATION FOR SEQ ID NO:7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Trp Xaa Arg Xaa Thr Xaa Xaa Xaa Lys Xaa Xaa Xaa Gln Xaa Xaa Arg
1               5                   10                  15
Xaa Xaa Leu Arg Xaa Xaa Xaa Xaa Tyr Tyr
            20                  25
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Arg Phe Asp Ser Asp Ala Glu Asn
1               5
```

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: unknown
        (D) TOPOLOGY: linear (ii) MOLECULE TYPE: cDNA (xi) SEQUENCE DESCRIPTION: SEQ ID NO:9:

```
GCGCTTCGAC AGCGACGCGG AGAAT                                    25
```

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: unknown
        (D) TOPOLOGY: linear (ii) MOLECULE TYPE: cDNA (xi) SEQUENCE DESCRIPTION: SEQ ID NO:10:

```
ATTCTCCGCG TCGCTGTCGA AGCGC                                    25
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Arg Glu Ala Val Ala Ala Pro Leu
```

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Arg Gly Ala Ala Ala Ala Pro Leu
1               5
```

( 2 ) INFORMATION FOR SEQ ID NO:13:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Glu Arg Ile Thr Gln Ile Ala Lys Gly Gln Glu Gln Trp Phe Arg Val
1               5                   10                  15
Asn Leu Arg Thr Leu Leu Gly Tyr Tyr
            20                  25
```

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Glu Arg Glu Thr Gln Ile Ala Lys Gly Asn Glu Gln Ser Phe Arg Val
1               5                   10                  15
Asp Leu Arg Thr Leu Leu Arg Tyr Tyr
            20                  25
```

( 2 ) INFORMATION FOR SEQ ID NO:15:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Asp Met Ala Ala Gln Ile Thr Arg Arg Lys Trp Glu Gln Ser Gly Ala
1               5                   10                  15
Ala Glu His Tyr Lys Ala Tyr Leu Glu
            20                  25
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:16:

```
Ala Ala Glu His Tyr Lys Ala Tyr Leu Glu Gly Glu Cys Val Glu Trp
1               5                   10                  15
Leu His Arg Tyr Leu Lys Asn Gly Asn
                20                  25
```

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gly Glu Val Thr Leu Arg Cys Trp Ala Leu Gly Phe Tyr Pro Ala Asp
1               5                   10                  15
Ile Thr Leu Thr Trp Gln Leu Asn Gly
                20                  25
```

CLASS I MHC MODULATION OR SURFACE RECEPTOR ACTIVITY

This invention was developed in part with grants ROI-CA 37099 and ROI-CA 35227 from the United States Government.

INTRODUCTION

This application is a continuation of application Ser. No. 07/649,471, filed 1 Feb. 1991, now abandoned, which is a continuation-in-part of application Ser. No. 323,565 filed Mar. 14, 1989, now abandoned, which is a continuation-in-part of application Ser. No. 028,241 filed Mar. 20, 1987, now abandoned.

TECHNICAL FIELD

The field of the subject invention concerns modulation or surface membrane responses.

BACKGROUND

The major histocompatibility complex (MHC) Class I antigens are expressed on virtually all types of vertebrate cells examined. These highly polymorphic transmembraneous glycoproteins have a 45 kD heavy chain consisting of a short cytoplasmic C-terminal tail, a transmembraneous region, and an extracellular N-terminal sequence which encompasses three domains, $\alpha_1$- and $\alpha_2$-domains carry all the immunological polymorphism, while the membrane-proximal $\alpha_3$ is non-covalently associated with the 12 kD $\beta_2$ microglobulin.

The MHC Class I antigen plays an essential role in restriction of the target cell repertoire of cytoxic T-lymphocytes (CTL), which involves preferential utilization of the different polymorphic MHC Class I antigens, H-2K, -D or -L (for mouse) or HLA-A, -B, or -C (for human), e.g. in recognition of viral infected cells. For the most part, attention has been directed to the role of the MHC Class I antigens in restricting T-cell activity. However, some authors have suggested a broader role for the antigens, which will be discussed below.

RELEVANT LITERATURE

For a review of biological functions of MHC Class I antigens see Ohno, *Immunol. Rev.* (1977) 33:59–69; and Simonsen, *Prog. Allergy* (1985) 36:151–176. For a description of the insulin receptor see Cuatrecasas, *Biol. Chem.* (1972) 247:1980–1991; Kasuga et al., ibid. (1983) 258:10392–10399; and Kasuga et al., ibid. (1983) 258:10973–10980. For suggestion that Class I antigens and insulin receptors interact, see Olsson, In *Cell Fusion: Gene Transfer and Transformation* (eds. Beers & Bassett) 395–403 (Raven Press, New York, 1984); Simonsen and Olsson, *Ann. Immunol.* (1983) 134D:85–92. A relationship between receptors and their specific ligands, where the reverse complement of limited regions in receptor mRNA are identified in the ligand DNA sequence is described by Bost et al., *Proc. Natl. Biochem. Biophys. Res. Commun.* (1985) 128:1373–1380. Other evidence supporting the interaction between MHC products and insulin receptor may be found in Fehlman et al., Phillips et al., ibid. (1986) 83:3474–3478; Due et al., ibid. (1986) 83:6007–6001, and Samson et al., *J. Immunology* (1986) 137:2293–2298. Suggestions of a correlation between overexpression of certain Class I products and increased metastatic potential of particular tumors may be found in Wallich et al., *Nature* (1985) 315:301–305; Katzav et al., *Int. J. Cancer* (1984) 33:47–415; Olsson, *Cancer Rev.* (1986) 3:91–114; and Goodenow et al., *Science* (1985) 230:777–783.

A structural association between epidermal growth factor receptor (EGFR) MHC Class I on human cells has been suggested by Schreiber et al., *J. Cell Biol.* (1984) 98:725–731 and Phillips et al., *Proc. Natl. Acad. Sci. USA* (1986) 83:3474–3478. A review of EGFR and its functions may be found in Carpenter and Cohen, *Ann. Rev. Biochem.* (1979) 48:193–216 and Carpenter, *J. Cell Sci. Suppl.* (1985) 3:1–9.

SUMMARY OF THE INVENTION

Methods and compositions are provided for modulating activity of cell surface receptors. The methods employ up or down regulation of cellular production of MHC Class I antigens or employ agonist or antagonist substances for non-covalent binding to the cellular receptor or MHC Class I antigen to affect the complexation between the MHC Class I antigen and the cellular receptor or mimic the effect of the Class I antigen. The methods and compositions may be used in diagnosis and therapy.

DESCRIPTION OF SPECIFIC EMBODIMENTS

Methods and compositions are provided for modulating the response of cell surface receptors by varying the interaction between the cell surface receptor and MHC Class I antigen. The variation may be as a result of up or down regulation of Class I antigen production or concentration at the surface, providing agonists or antagonists for mimicking the non-covalent binding of the Class I antigen to the receptor or inhibiting such binding. Modulation of the Class I antigen-receptor interaction can be used in diagnosing and treating a large variety of conditions associated with cellular membrane receptors.

Human MHC Class I antigens are HLA-A, B, C, Qa and Tl. Of particular interest involved with the modulation of cellular receptors are the HLA-B and -C antigens, particularly the $\alpha_1$- and $\alpha_2$-domains, more particularly the $\alpha_1$-domain.

Of particular interest are the amino acid sequences involved in the polymorphic regions of $\alpha_1$- and $\alpha_2$-, ranging from amino acid 50 to amino acid 90, more particularly amino acids 55 to 90, usually 60 to 90, more particularly 65 to 90 or 90 to 120, more usually 90 to 116, where the amino acid sequences of interest are usually in the C-terminus of the $\alpha_1$-domain and N-terminus of the $\alpha_2$-domain. The region 60–85, more particularly 65 to 85 or 70 to 85 are found to be of particular interest.

It is found that the amino acids from 83 to 85 may be of particular significance. For both MHC Class I D and K, or analogous HLA-B or C, the sequence is R Y Y. Peptides of particular interest will comprise this sequence and may include at least about 20, usually at least about 15, and preferably nor more than about 10 amino acids on either side of the sequence, preferably having at least 5 amino acids at the N-terminal side, and more preferably not having more than about 5-amino acids at the C-terminal side. The presence of two tyrosines is particularly desirable for the insulin receptor and epidermal growth factor receptor.

Desirably, the total number of amino acids will not exceed 20, preferably not exceed about 18, more preferably not exceed about 15 with the sequences indicated above, but increasing the extent of the sequence does not affect the activity, primarily affecting the ability to synthesize.

Also of interest is the region from about amino acid 30 to amino acid 45, more particularly 32 to 40, particularly an oligopeptide of at least four amino acids, more usually at least about six amino acids, and preferably at least about eight amino acids, where the sequence includes a tetramer involving an acidic amino acid and a basic amino acid separated by one neutral amino acid, particularly a neutral amino acid of at least five carbon atoms and one of the acidic or basic amino acids is flanked by a neutral amino acid. Of particular interest is where the intervening neutral amino acid is an aromatic or aliphatic hydrocarbon amino acid, e.g. glycine or phenylalanine.

A large number of surface membrane proteins are involved with the transduction of signals and serve as receptors for a wide variety of ligands. For the most part, receptors are defined by the ligand which activates the receptor for transduction or serves to endocytose the ligand. These receptors include endocrine, paracrine and autocrine receptors, adrenergic receptors, lipoprotein receptors, opiate receptors, and steroid receptors. These receptors include surface protein receptors for asialoglycoprotein, insulin, somatostatin, somatotropins, growth factors, such as growth hormone, platelet derived growth factor, insulin like growth factor, epidermal growth factor, α-transforming growth factor, nerve growth factor, fibroblast growth factor, somatomedin, vasopressin, prostaglandins, eosinophil chemotactic factor, acetylcholine, thyroxine (TSH), epinephrine; endorphins, enkephalins and dynorphin; neurotensin, oxytocin, transferrin, substance P, lymphokines, such as 1-, 2-, 3- and 4-, etc.; colony stimulating factors, such as GM-CSF, M-CSF, G-CSF, etc; lipoproteins, such as low density lipoprotein; and steroids, such as estrogen, androgen, glucocorticoids, corticosteroids, etc. Of particular interest are receptors which are cycled, that is, internalized into the cytoplasm and optionally returned to the plasma membrane surface. Illustrative of these receptors are the receptors for insulin, EGF, LDL, transferrin, interleukins, and asialoglycoprotein.

Modulation of the MHC Class I antigen activation can be achieved in a variety of ways. The number of MHC antigen molecules at the surface can be increased or decreased by employing compounds which activate or inhibit the Class I antigen production. These compounds include interferon, dimethyl sulfoxide (DMSO), tetradecylphorbyl acetate (TPA), and retinoid acids. Alternatively, one may modulate the complex formation by employing antibodies to the $\alpha_1$- or $\alpha_2$-domain, particular the $\alpha_1$-domain, which inhibit the interaction action between the Class I antigens and the receptor. Either polyclonal or monoclonal antibodies may be employed, particularly monoclonal, Alternatively, one may employ the monoclonal antibodies specific for the $\alpha_1$-domain to be used as immunogens for the production of anti-idiotype antibodies, which will mimic the conformation of the Class I antigen epitope to which the monoclonal antibody binds. Thus, the anti-idiotype may act as a substitute Class I antigen and may serve to block autoimmunity. The whole antibodies need not be employed, the variable region sufficing, or larger fragments such as Fab or F(ab')2, Fab', etc.

The antibodies may be prepared in accordance with conventional ways. Particularly, the Class I antigen may be used as an immunogen and injected into an appropriate host, conveniently a mouse, for initiating an immune response. One or more booster injections may be employed at two or more week intervals. Two to three days after the last injection, the animal host may be sacrificed, the spleen isolated, and the B-lymphocytes immortalized. Various techniques exist for immortalization, conveniently fusion with a myeloid cell, followed by selecting for hybridomas and screening under limiting dilution conditions for hybridomas producing antibodies having the desired characteristics. Thus, in the present situation the Class I antigen could be used for screening or the antibody to the domain of interest in the case of the anti-idiotype.

Instead of employing antibodies, oligopeptides may be employed which are capable of mimicking the site of the Class I antigen associated with binding to the receptor or the receptor site which binds to the Class I antigen. Thus, by preparing oligopeptides having a sequence substantially conforming to a sequence of the binding domain of the Class I antigen, or active fragment thereof, one can substitute for the presence of the Class I antigen by using the oligopeptide for activation of the receptor. By modifying the sequence, for example by substitutions, deletions or insertions, where usually from 1 to 3, usually from 1 to 2, amino acids are involved, enhanced binding of the peptide to the receptor may be achieved.

By non-conservative substitutions are intended those substitutions which substantially differ as to polarity and/or size, where each of the lines in the following table indicates what are conservative substitutions.

TABLE A

| Neutral | |
|---|---|
| Aliphatic | |
| Non-polar | |
| small | G, A (P) |
| large | V, I, L |
| Polar | |
| Oxy or Thio | S, T, C, M |
| Amide | N, Q |
| Aromatic | F, W, H, Y |
| Charged | |
| Acidic | D, E |
| Basic | K, R |

( ) intends that the amino acid will normally not be used as a substitute for others on the same line.

It is found that the peptides which bind to the receptors enhance receptor activity. While not wishing to be bound to the theory, it appears that the peptides are involved with inhibiting internalization of the receptor. In this manner, the lifetime of the ligand-receptor complex is extended, so that one observes an enhanced activity as a result of binding of the ligand to the receptor. In addition, there may be other effects of the peptide, such as allosteric effects, which may enhance binding affinity, activation effects, where the peptide results in activation of the receptor, so as to provide for transduction of a signal into the cytoplasm, or other effect, where the sum total of the result is an enhanced effect as compared to the absence of the peptide or MHC binding to the receptor.

In a variety of disease states, disease is as a result of a reduced presence of a particular receptor at the surface or lower affinity for the ligand. In this situation, one could reduce the density of the Class I MHC antigen or provide for the peptide at an appropriate concentration, which allows for activation of the receptor. Conditions such as diabetes, Graves disease, arthritis, ankylosing spondylitis, Reiter's disease, analgesia, viral disease, etc., could be associated with inadequate receptor response.

Alternatively, in other situations, one might wish to down regulate receptor binding, where one wishes to diminish the receptor response. Illustrative of such conditions is neoplasia, arthritis, lupus erythematosus, etc., where it is desirable to reduce the response to growth factors or other secreted factors, which encourage proliferation or other undesirable response. In this situation, one could treat the target cells with a drug which would enhance the population of Class I antigens at the surface.

The subject peptides may affect one activity of the receptor differently from a different activity. For example, while with the insulin receptor, glucose uptake is enhanced, the tyrosine kinase activity is diminished. Thus, the subject peptides may selectively modify a receptor having a plurality of activities.

Instead of a change in the MHC Class I antigen population at the surface, the effective concentration of Class I antigen for complexing with receptors may be reduced. It is noted that viral infections deplete Class I antigens at the surface and in appropriate situations may be used for this purpose. As already indicated, Class I antigen depletion could also be achieved using antibodies or oligopeptides which bind to the Class I antigen at or near the complexing site inhibiting complexation with the receptor or bind to the receptor at or near the complexing site inhibiting complexation with the Class I antigen. These compounds can be prepared by employing sequences comparable to polymorphic sequences, particularly in the $\alpha_1$-domain of the Class I antigen, more particularly HLA-B or -C antigens (mouse H-2L or D).

Of particular interest are oligopeptides comprising at least a portion of one of the following sequences, where the oligopeptides comprise as the active sequence, at least six amino acids, usually at least eight amino acids, more usually at least 12 amino acids, and fewer than 40 amino acids, more usually fewer than 30 amino acids, preferably, not more than about 25 amino acids, preferably being from about 8 to 25 amino acids, more preferably about 8 to 20 amino acids. It is understood that up to five, more usually up to about three substitutions or deletions may be made in the subject sequences, where the change will not be more than about 20 number %, usually not more than about 10 number % of the number of amino acids in the active sequence. Also the following sequences may be joined together either contiguously or by bridges of not more than about 20 amino acids, more usually not more than about 10 amino acids. Furthermore, where the sequences overlap, it is intended that the overlapping sequences not be repeated, but rather the non-overlapping sequences be joined in proper sequence.

The oligopeptide will have at least six amino acids which are the same or substantially the same as a sequence included in the following sequence.

1. D T $aa^{32}$ F V R F D S D $aa^{40}$ $aa^{41}$ (SEQ ID NO:1)
2. F V R F D S D $aa^{40}$ $aa^{41}$ S P R $aa^{45}$ (SEQ ID NO:2)
3. W $aa^{52}$ E Q $aa^{55}$ $aa^{56}$ G P E Y W (SEQ ID NO:3)
4. W $aa^{61}$ $aa^{62}$ $aa^{63}$ T $aa^{65}$ $aa^{66}$ $aa^{67}$ K $aa^{69}$ $aa^{70}$ $aa^{71}$ Q (SEQ ID NO:4)
5. W $aa^{61}$ $aa^{62}$ $aa^{63}$ $aa^{64}$ $aa^{65}$ $aa^{66}$ $aa^{67}$ K $aa^{69}$ $aa^{70}$ $aa^{71}$ $aa^{72}$ $aa^{73}$ $aa^{74}$ $aa^{75}$ $aa^{76}$ $aa^{77}$ $aa^{78}$ $aa^{79}$ $aa^{80}$ $aa^{81}$ $aa^{82}$ $aa^{83}$ $aa^{84}$ $aa^{85}$ (SEQ ID NO:5)
6. E Q $aa^{73}$ $aa^{74}$ R V $aa^{77}$ $aa^{78}$ R $aa^{80}$ $aa^{81}$ $aa^{82}$ R Y Y (SEQ ID NO:6)

wherein:
$aa^{32}$ is any neutral aliphatic amino acid of from 4 to 6 carbon atoms particularly N, Q, V, I, or L, more particularly Q or L;

$aa^{40}$ is an aliphatic amino acid, charged or uncharged, usually non-polar or acidic of from 2 to 5, more usually 2 to 4 carbon atoms, particularly G, A, P, D or E, more particularly A or D;

$aa^{44}$ is P, N, or Q, particularly P or Q;

$aa^{45}$ is any aliphatic amino acid, particularly G, A, S, T, M, K, R, or E, particularly G, E, or K;

$aa^{52}$ is a neutral aliphatic amino acid of from 4 to 6 carbon atoms, particularly V, I, L or M, more particularly V or I;

$aa^{55}$ is any charged amino acid, particularly K, R, D, or E, more particularly K or E;

$aa^{56}$ is a charged amino acid, particularly D, E, K or R, more particularly E or K;

$aa^{61}$ is D or E;

$aa^{62}$ is K, R, G, or A, particularly R or G;

$aa^{63}$ is any aliphatic amino acid other than basic of from 4 to 6 carbon atoms, particularly D, E, I, L, V, N, or Q, more particularly E, N, or Q;

$aa^{64}$ is S, T, or M, particularly T;

$aa^{65}$ is any polar or basic amino acid of 4 to 6 carbon atoms, particularly N, Q, K or R, more particularly Q;

$aa^{66}$ is any aliphatic amino acid of from 4 to 6 carbon atoms, particularly L, I, V, K, R, N, or Q, more particularly K, I or N;

$aa^{67}$ is any neutral aliphatic or aromatic amino acid, particularly G, A, L, V, I, S, T, M, C F, Y, N, or Q, more particularly C, S, Y, or M;

$aa^{68}$ is K or R, particularly K;

$aa^{69}$ is any aliphatic neutral or acidic amino acid, particularly D, E, G, A, S, T, or M, particularly A or T;

$aa^{70}$ is any aliphatic amino acid, neutral, polar, or basic (other than acidic) from 3 to 6, usually 4 to 6 carbon atoms, particularly N, Q, K, R, S, or T, more particularly N, Q, or K;

$aa^{71}$ is any aliphatic amino acid other than basic, usually from 2 to 5 carbon atoms, particularly G, A, S, T, D, or E, more particularly A or T;

$aa^{72}$ is N or Q, particularly Q;

$aa^{73}$ is S, T, F, Y, H, or W, particularly T;

$aa^{74}$ is D, E, F, Y, H, or W, particularly Y or D;

$aa^{75}$ is K or R, particularly R;

$aa^{76}$ is an aliphatic amino acid other than basic of from 4 to 6 carbon atoms, particularly D, E, V, I, or L, more particularly E or V;

$aa^{77}$ is a polar aliphatic amino acid of from 3 to 6 carbon atoms particularly N, Q, S, T, D, or E, more particularly N, D or S;

$aa^{78}$ is a non-polar aliphatic amino acid of from 3 to 6 carbon atoms, particularly A, P, V, I, or L, more particularly L;

$aa^{79}$ is K or R, particularly R;

$aa^{80}$ is a neutral aliphatic amino acid of from 3 to 6 usually 4 to 6 carbon atoms, particularly, S, T, N, Q, I, V or L, more particularly N, J, or I;

$aa^{81}$ is an aliphatic non-polar amino acid, particularly G, A, L, I, or V, more particularly A or L;

$aa^{82}$ is an aliphatic amino acid other than acidic, of from 2 to 6, usually 5 to 6, carbon atoms, particularly K, R, G, A, L, I, or V, more particularly L or R;

$aa^{83}$ is an aliphatic amino acid other than acidic of from 2 to 6 carbon atoms, particularly K, R, G, A, L, I, or V, more particularly G or R;

$aa^{84-85}$ are aromatic amino acids, particularly F, Y, H, or W, more particularly Y.

Preferably, there will usually not be more than three mutations in the above sequence as substitutions, deletions, or insertions.

Of particular interest is an amino acid sequence of at least 6, usually at least 8, amino acids coming within the following sequence.

W D/E R $aa^{63}$ T Q/R $aa^{66}$ $aa^{67}$ K $aa^{69}$ $aa^{70}$ $aa^{71}$ Q T/W $aa^{74}$ R V/E $aa^{77}$ L R $aa^{80}$ L/A L/R G/R Y Y (SEQ ID NO:7)

wherein:

$aa^{63}$ is E, I, or N;

$aa^{66}$ is I, N, or K, particularly I;

$aa^{67}$ is A, C, S, M, or Y, particularly Y or C;

$aa^{69}$ is G, A, T, or P, particularly A or T;

$aa^{70}$ is Q, N, or K;

$aa^{71}$ is A, E, or T;

$aa^{74}$ is D, F, or Y, particularly D or Y;

$aa^{77}$ is N, S, or D;

$aa^{80}$ is I, N, or T.

where when two amino acids are indicated at a particular site, either amino acid may be employed interchangeably. Up to three of the amino acids may be subject to conservative or non-conservative changes, there being from 0 to 2 deletions or insertions of from 1 to 2 amino acids.

The oligopeptides may be provided in a variety of ways, being joined to non-wild-type flanking regions, as fused proteins, joined by linking groups or directly covalently linked through cystine (disulfide) or peptide linkages. The oligopeptides may be joined to a single amino acid at the N- or C-terminus or a chain of amino acids. The fused peptides may be extended to provide convenient linking sites, e.g. cysteine or lysine, to enhance stability, to bind to particular receptors, ease of purification, change the physical characteristics, e.g. solubility, charge, etc, stabilize the conformation, etc. The oligopeptide may be N- or C-terminal or internal.

The oligopeptide may be joined to the peptides for a variety of purposes. The oligopeptide may be linked through a variety of bifunctional agents, such as maleimidobenzoic acid, methyldithioacetic acid, mercaptobenzoic acid, S-pyridyl dithiopropionate, etc. The oligopeptides may be linked to proteins to provide immunogens for the production of antibodies. The oligopeptides may be linked, particularly by an intracellular cleavable linkage, to antibodies for site directed action. The oligopeptides may be linked to peptides to enhance stability, for site directed action, to provide additional physiological activity or the like. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

The oligopeptides may also be modified by incorporation into the lumen of vesicles, e.g. liposomes, which in turn may be bound to ligands or receptors for direction to particular cells or tissue.

The oligopeptides may be used as ligands to determine the presence of particular receptors as a diagnostic. Thus, cells could be screened, intact or as a lysate, for the population of one or more receptors which bind the oligopeptide. The oligopeptides could be labeled, directly or indirectly, with a label which provides a detectable signal, e.g. radioisotope, fluorescers, enzyme, particle, chemiluminescer, etc. Thus, cells from tissue, e.g. biopsies, blood, or the like may be diagnosed in vitro or in vivo for the presence of receptors binding to the oligopeptides. In addition, the binding pattern with the MHC Class I antigen of various cells can be determined. Diseased states as a result of inadequate complexation between MHC Class I antigens and receptors can be determined. A large number of protocols are known and have been developed and appear in the patent and scientific literature. Commercially available assays include ELISA, EMIT, SLFIA, RIA, etc.

The oligopeptides may be employed in a variety of ways. For therapy, they may be administered parenterally, e.g. by injection at a particular site, for example, subcutaneously, intraperitoneally, intravascularly, or the like.

The formulations will usually involve a physiologically acceptable medium, such as deionized water, saline, aqueous ethanol, phosphate buffered saline, and the like. The manner of formulation will vary depending upon the purpose of the formulation, the particular mode employed for modulating the receptor activity, the intended treatment, and the like. The formulation may involve capsules, liposomes, time delayed coatings, pills, or be formulated in pumps for continuous administration. Because of the wide variety of modes of treatment, the varying responses, the different disease states, or the like, no useful limits may be given for the concentration of the active components. These can be determined empirically in accordance with known ways. See, for example Harrison's, Principles of Internal Medicine, 11th ed. Braunwald et al. ed, McGraw Hill Book Co., New York, 1987.

The oligopeptides of this invention may be prepared in accordance with conventional techniques, such as synthesis, recombinant techniques, or the like. See, for example, Maniatis et al., Molecular Cloning: A laboratory manual, CSH Laboratory, Cold Spring Harbor, N.Y., 1982; use of a Beckman Model 990 peptide synthesizer or other commercial synthesizer.

The following examples are offered by way of illustration and not by way of limitation.

EXPERIMENTAL

Mutant line, R1E, derived from the murine thymoma line R1 by chemical mutagenesis (Parnes and Seidman, *Cell* (1982) 29:661–669; Allen et al., *Proc. Natl. Acad. Sci. USA* (1986) 83:7447–7451) expresses in contrast to R1, none of the parental $H2^k$ haplotype antigens of the C58 strain of origin due to the lesions induced in the $\beta_2$-microglobulin ($\beta$2m) gene in R1E. Specific insulin binding to R1E murine thymoma cells and various R1E transfectants was determined, with the binding being performed as described in Gavin et al., *J. Biol. Chem.* (1973) 248:2202–2207 and Due et al., *Diabetologia* (1985) 28:749–755.

All cells were cultivated in RPMI-1640 with 15% fetal calf serum (FCS) and with the various additives as indicated (Allen et al., supra (1986)). Prior to insulin binding assays, the cells were seeded in RPMI-1640 with 10% FCS and at a density of $2\times10^4$ cells/ml, harvested three days later, viability assured to be >95% by trypan dye exclusion, and the cells subsequently resuspended in assay buffer for insulin binding at a concentration of $7.5\times10^7$ cells/ml. $^{125}$I-labeled human insulin in a final concentration of 50 pM (labeled in the A14 position and obtained from NOVO A/S Denmark) was added and the cell incubated for 90 minutes at 18° C. in a shaking waterbath. Two ml ice-cold assay buffer were added at the end of incubation, the cells centrifuged at 300 g for 5 minutes, at 100 g for 10 minutes, and the amount of $^{125}$I-insulin in the pellet counted in a γ-counter. Non-specific binding was estimated as the amount of $^{125}$I-insulin binding in the presence of $10^{-6}$M unlabeled insulin, and specific insulin binding calculated as the difference in binding of $^{125}$I-insulin with and without unlabeled insulin. Specific binding <1% was estimated to be non-specific considering the Scatchard plots and the specific binding as related to cell number.

Scatchard plots were done for lines R1, R1E, R1E/β2m, R1E/D$^b$, R1E/β2m/K$^b$, R1E/β2m/D$^b$, R1E/β2m/D$^b$δ, and R1E/β2m/D$^b$—(1+2) with $3\times10^7$ cells per sample and each point representing duplicate or triplicate samples. The Scatchard plots were repeated 3–10 times for each determination. Only R1 and R1E/β2m/D$^b$ displayed applicable amounts of insulin receptor (IR). The curve observed shows that in addition to high affinity IR, these cells also have appreciable amounts of receptors with lower affinity for insulin, which may to some extent be due to indirect effects of transfection and/or co-expression of other insulin binding receptors such as those for IGF-I (Rechler and Hessley In *Polypeptide Hormone Receptors* (ed B. I. Posner) pp 227–297, Marcel Dekker, New York (1985)).

R1 murine thymoma cells have a cell surface density of IR comparable to other lymphocyte cell populations in contrast to the human IM-9 cell line often used for insulin assays, and which is an Epstein-Barr virus transformed line with exceptionally high amounts of nonfunctional IR. It was accordingly necessary in the R1/R1E system to use comparatively high amounts of cells per sample. Titration of specific insulin binding as related to cell number demonstrated that the optimal cell number per sample for specific insulin binding was $7\times10^7$ cells—impractical to use on all Scatchard plots. The curves for R1 and R1E/β2m/K$^b$ show that these two lines did not express significant amounts of IR.

Insulin receptor mRNA in R1, R1E and R1E transfectants was determined as follows. Total RNA was isolated from cells as per Chirgwin et al., *Biochemistry* (1979) 18:5294–5299, and poly A+ RNA selected as per Maniatis et al., *Molecular Cloning: A Laboratory Manual* CSH Laboratory, Cold Spring Harbor, N.Y., (1982). For Northern blot analysis 5 μg of poly A+ selected murine liver mRNA was fractionated on a 1.0% agarose-formaldehyde gel (Church and Gilbert, *Proc. Natl. Acad. Sci. USA* (1984) 81:1991–1995) and blotted on a Zeta-probe nylon membrane (BioRad Laboratories, Richmond, Calif.). Insulin receptor-specific sequences were detected by hybridization with a synthetic DNA oligonucleotide representing amino acids 732–741 inferred from the insulin receptor cDNA precursor (Ullrich, et al., *Nature* (1985) 313:756–761). Hybridization and washing conditions were as per Church and Gilbert, supra (1984), except that hybridization and washes were at 45° C. Approximately 1 μg and 1:10 dilution of poly A+ selected mRNA from mouse liver and appropriate cell lines was spotted on the Zeta-Probe membranes and hybridized as above. Molecular weight markers for Northern blot analysis were purchased from Bethesda Research Laboratories (Bethesda, Md.). A predominant species of 4.8 kb from mouse liver hybridized to the human insulin receptor oligonucleotide. This species was also noted by Ullrich et al., supra (1985), in human placental mRNA with radiolabeled cloned human insulin receptor cDNA sequences.

The surface proteins of the various cell lines were screened using fluorescent labeled monoclonal antibodies and a FACS.

TABLE 1

Fluorescence-Activated Cell Sorter (FACS) Analysis R1, R1E and the Transfectants for Expression of H-2 and b

| Cell Lines[c] | H-2 specificity monoclonal antibodies[a] | K$^k$D$^k$ (28-8-6) | K$^k$ (11.4) | K$^b$ (20-8-4) | D$^k$ (15-5-5) | D$^b$ (28-14-8) | b2m[b] | b2m |
|---|---|---|---|---|---|---|---|---|
| R1 | | 750 | 505 | <10 | 435 | 16 | <10 | 175 |
| R1E | | 25 | <10 | <10 | <10 | <10 | <10 | <10 |
| R1E/b2m | | 290 | 80 | 15 | 90 | 15 | 225 | 80 |
| R1E/D$^b$ | | 145 | 30 | <10 | 30 | 570 | <10 | <10 |
| R1E/b2m/D$^b$ | | 370 | 115 | 10 | 170 | 1240 | 450 | 390 |
| R1E/b2m/K$^b$ | | 400 | 215 | 410 | 260 | <10 | 510 | 425 |
| R1E/b2m/Dd | | 345 | 170 | 10 | 320 | 250 | 200 | 105 |
| R1E/D$^b$ − (1 + 2) | | 190 | 70 | <10 | 50 | 825 | <10 | <10 |
| R1E/b2m/D$^b$ (1 + 2) | | 350 | 105 | 10 | 130 | 880 | 210 | 160 |

Legend to Table 1

[a] The monoclonal antibodies have been described previously (Ozato et al., *Transplantation* (1982) 34:113–120). For staining, $10^6$ cells were incubated with 1 μg antibody/ml at 4° C. with fluoresceinisothiocyanate (FITC) conjugated rabbit anti-mouse polyclonal antibody (purchased from DAKO, Denmark). The cells were washed twice in PBS and analyzed. Cells incubated with FITC-conjugated secondary antibody served as negative controls. A shift of >15 channel numbers on the linear fluorescence scale was considered significant; all samples were analyzed both on a logarithmic and linear fluorescence scale. The absolute number of bound FITC molecules per cell was estimated as described (Due et al., supra, (1985)). It should be noted that comparison of FACS data to estimate the relative proportion of different H-2 molecules only is reasonable, when the same primary antibody is used.

[b] Expression of H-2 was for all lines examined both by solid phase radioimmunoassay (RIA) with $^{125}$I-labeled protein A as secondary reagent and by FACS as described above. Briefly, RIA assays (Weiss et al., *Nature* (1984) 310:650–655) were done by plating $5\times10^5$ cells (96 well microtiterplate) in 50 μl diluted antibody in MEM+10% FCS was then added. The cells were incubated 4 hours at 4° C., pelleted and washed with MEM+10% FCS. $^{125}$I-Protein A was added (Amersham) to 100,000 cpm and incubated for 16 hours at 4° C. Cells were pelleted and washed three times with MEM+10% FCS before counting in a Beckman Gamma Counter. All samples were done in duplicate and with less than 5% variation on all samples counted.

c The R1, R1E lines, the H-2K and H-2D genes, and the procedures for transfection have been described in detail previously (Allen et al., *Proc. Natl. Acad. Sci. USA* (1986) 83:7447–7451; Goodenow et al., *Science* (1982) 215:677–679). The various designations indicate: R1E/β2m, transfected with $\beta 2^b$, R1E/K$^b$; transfected with K$^b$; R1E/β2m/K$^b$, transfected with β2m and K$^b$; R1E/β2m/D$^b$ transfected with β2m and D$^b$;, but the D$^b$ cell surface antigen was down-regulated with monoclonal antibody to D$^b$; R1E/β2m/D$^b$-(1+2), transfected with β2m and truncated D$^b$ gene, only expressing the α3-domain on the cell surface; R1E/D$^b$-(1+2), transfected with truncated D$^b$, only expressing the α3-domain.

Adenocarcinoma cell line LT85 (Callahan et al., *J. Immunol.* (1983) 471–474) lacks appreciable cell surface expression of the H-2 antigens characteristic of the strain of derivation. Interferon-α (IFN-α) treatment significantly increases the cell surface density of both H-2K$^k$, H-2D$^k$ and increases in parallel the specific binding of insulin. Alternatively, the ultraviolet light-induced fibrosarcoma LR335 (Daynes et al., *Transplantation* (1977) 23:343–348), unlike R1E or LT85, expresses appreciable levels of the H-2K$^k$ antigen, endogenous to the strain of origin with negligible H-2D$^k$, unless induced with IFN. As shown in Table 2, IFN treatment markedly increases both H-2D$^k$ expression and the binding of insulin, approaching the levels of the other positive cell lines tested.

TABLE 2

Effect of Interferon on MHC Class I and Insulin Receptor Expression

| Cell Line | Interferon Treatment | H-2 allele Expression$^a$ | | Specific Insulin Binding (%) |
|---|---|---|---|---|
| | | K$^k$ (16-1-11) | D$^k$ (15-5-5) | |
| LT85 | None | 3,370 | 1,030 | 2.0 |
| | + | 19,170 | 6,500 | 3.2 |
| LR 335 | None | 16,230 | 1,000 | <1.0 |
| | + | 28,770 | 6,639 | 2.1 |

$^a$Estimated by radioimmunoassay as described in Table 1 and the results given as cpm/5 × 10$^5$ cells
$^b$The interferon treatment was done with alpha-interferon.

To map the control of insulin receptor in a third haplotype, several Class I variants of the BALB/c S49 thymoma line (Joseph et al., *J. Immunol.* (1986) 137:4016–4020) were tested for insulin binding. As shown in Table 3, the H-2K/H-2D positive variant displayed significant hormone binding relative to the H-2K minus variant, suggesting that the D molecules support the cell surface expression of the receptor. The homology shared between H-2D$^b$ and H-2L$^d$ suggest that the H-2L locus also exerts an interaction with the IR.

TABLE 3

Expression of MHC Class I and Insulin Receptor in Six Murine Cell Lines of Two Different Haplotypes

| MHC Class I Expression$^b$ | Cell lines$^a$ | | | | | |
|---|---|---|---|---|---|---|
| | 3LL/G2 | 3LL/G4 | 28 | 33 | 36 | 29 |
| K$^b$ (20-8-4) | 14,840 | 2,500 | — | — | — | — |
| D$^b$ | 3,130 | 7,440 | — | — | — | — |
| (28-14-8) K$^d$ (20-8-4) | — | — | 3,572 | 1,124 | 940 | 292 |
| D$^d$ (34-1-2) | — | — | 4,930 | 661 | 278 | 280 |
| L$^d$ (28-14-8) | — | — | 559 | 297 | 261 | 341 |
| K$^k$ (negative control; 11.4) | — | — | 254 | 297 | 286 | 595 |
| Specific Insulin Binding (%) | 2.4 | 5.0 | 3.1 | 1.8 | <1.0 | <1.0 |

$^a$All cell lines have been described elsewhere (Olsson and Forchhammer, Proc. Natl. Acad. Sci. USA (1984) 81:3389-3393; Joseph et al., J. Immunol. (1986) 137:4016–4020). The lines numbered 28, 33, 36, and 29 have previously been designated S49.1, S49.2, S49.3, and S49.4, respectively.
$^b$Estimated by RIA (see Table 1) with monoclonal antibodies as indicated and the data given as cpm/5 × 10$^5$ cells.

Study of MHC Class I Peptide

MATERIAL AND METHODS

Cell Culture

All cell lines are grown in minimal essential medium (MEM, Gibco) supplemented with 2 mM glutamine, 50 U/ml penicillin, 50 μg/ml streptomycin, 1.0% nonessential amino acids, 1 mM sodium pyruvate and 10% fetal bovine serum (Hyclone) excepting R1E and R1E transfectants which are grown in RPMI (Gibco) and supplemented as above. The following cell lines are used in this study: P815—a murine mastocytoma of H-2$^d$ origin; R1E and related transfectants—murine lymphomas of H-2$^k$ origin but transfected with H-2$^b$ genes (Allen et al., (1986)); human lymphoblastoid lines #1 and #2-Epstein-Barr virus transformed lymphocytes from two related individuals, #2 being a Type I diabetic; LR335—a UV induced murine fibrosarcoma of H-2$^k$ origin.

Hormone Binding

Hormone binding assays are based on descriptions by Freychet *Diabetologia* (1976) 12(2):85–100; and Freychet et al., *Endocrinology* (1977) 100:115–121 with modifications. All reactions are carried out in 200 μl volumes in 96-well, round-bottomed microtiter plates (Dynatech Labs, Va.) in MEM (Gibco) with 0.5% bovine serum albumin (Sigma fraction V) and 0.1% sodium azide to prevent internalization and subsequent degradation of membrane proteins. Sodium azide at 0.1% does not alter insulin binding. Cells are resuspended at 1×10$^7$ to 1×10$^8$, depending on the cell type and, when appropriate, pre-incubated at 4° for one hour in the presence of peptide at 100 μg/ml. Specific insulin binding is measured using $^{125}$I-insulin (Amersham, 2000 Ci/mole, 370 kBq/10 μCi) as tracer at 50–100 pM. Incubation is carried out for 90 minutes at 20°. Cells are then washed three times in ice-cold MEM to remove unbound insulin and the pellets resuspended to 100 μl and counted in a Beckman gamma counter. Non-specific insulin binding is measured in the presence of 100 μg/ml unlabeled porcine insulin (Sigma). Specific EGF binding is measured in a similar fashion using $^{125}$I-EGF (Amersham, 150 μCi/mg) as tracer and unlabeled mouse submaxillar gland EGF (Sigma) at 1 μg/ml is used as cold competitor.

RESULTS

Enhanced Insulin Binding Mediated by an MHC Class I Peptide

To investigate H-2/IR interactions on the cell surface, a peptide was synthesized corresponding to the α1 domain, aa[61-85], of the H-2L$^d$ protein. The sequence is E-R-I-T-Q-I-A-K-G-Q-E-Q-W-F-R-V-N-L-R-T-L-L-G-Y-Y (SEQ ID NO:13).

When increasing amounts of this peptide were added to cells in culture, the synthetic Class I analogue significantly boosted the hormone binding on P815 mastocytoma cells in a dose-dependent fashion. Whereas the peptide was able to enhance receptor activity by at least an order of magnitude, peptides of similar size representing sequences from a T-cell receptor or MHC Class II sequences failed to augment the levels of hormone binding on P815. In addition, an H-2L$^d$ peptide synthesized without glutamic at position 71, but otherwise identical to L$^d$ 61-85, also was unable to affect insulin binding, demonstrating the exquisite specificity of this peptide for the receptor.

Several other cell types were tested for L$^d$ peptide enhancement of insulin binding, including freshly isolated murine spleen. (See Table 4) Cells of both human and murine origin demonstrated insulin binding augmentation to varying degrees by the L$^d$ peptide. The magnitude of induction on BALB/c spleen cells supports the in vivo effect of the peptide.

TABLE 4

Effect of L$^d$ Peptide on Cell Types/Hormone Receptors

| Cell Type/Line | Origin | Hormone | cpm$^{125}$I-Insulin (% Bound/Free) | | Relative Fold Increase with Peptide |
|---|---|---|---|---|---|
| | | | L$^d$ Peptide | No Peptide | |
| BALB/c Spleen | murine | insulin | 2,803 (6.0) | 163 (.04) | 150 |
| P815 Mastocytoma | murine | insulin | 1,223 (2.0) | 95 (.15) | 13.3 |
| Lymohoblastoid #1 | human | insulin | 5,905 (13) | 3,743 (8.0) | 1.6 |
| Lymphoblastoid #2 | human | insulin | 2,409 (5.0) | 1,306 (3.0) | 1.7 |
| LR 335 Fibrosarcoma | murine | EGF | 2,394 (3.8) | 2,543 (4.1) | 0 |

Insulin binding on various cell types in the presence and absence of Class H-2L$^d$ peptide. All cell lines are described above. Cells were pre-incubated with or without the L$^d$ peptide, aa[61-85] and specific $^{125}$I-insulin binding was measured as described in Methods. When two non-Class I peptides, murine T-cell receptor and murine Class II peptide were used instead of the L$^d$ peptide, results were similar to no added peptide. Results are expressed as bound cpm of $^{125}$I-insulin and the percent of counts Bound/Free $^{125}$I-insulin.

Furthermore, no effect was observed when epidermal growth factor (EGF) binding was measured on a fibrosarcoma expressing EGF receptors, showing further specificity for the peptide in interacting with insulin receptors.

Additional insulin binding studies were carried out on a series of related cells possessing different surface expression profiles of Class I/IR complexes. The insulin binding level on RIE, RIE+β2M+D$^b$ were tested in the presence and absence of L$^d$ peptide. The H-2L$^d$ peptide was capable of augmenting the IR found on the D$^b$ transfectants alone—both RIE and RIE+β2M+K$^b$ failed to show appreciable L$^d$ peptide induced enhancement in insulin binding.

TABLE 5

Effect of L$^d$ Peptide on Insulin Binding on RIE, RIE + β2M + Dβ, RIE + β2M + Kβ

| | cpm $^{125}$I-Insulin (% B/F) | |
|---|---|---|
| Cell Line | L$^d$ Peptide | No Peptide |
| RIE | 752 (1.0) | 393 (1.0) |
| RIE + β2M + D$^b$ | 935 (2.0) | 471 (1.0) |

TABLE 5-continued

Effect of L$^d$ Peptide on Insulin Binding on RIE, RIE + β2M + Dβ, RIE + β2M + Kβ

| | cpm $^{125}$I-Insulin (% B/F) | |
|---|---|---|
| Cell Line | L$^d$ Peptide | No Peptide |
| RIE + β2M + K$^b$ | 478 (1.0) | 432 (1.0) |

In agreement with the previous observations, the H-2k$^d$ transfectants appear to lack cell surface IR since no appreciable hormone binding could be induced with the peptide. Consequently, these data confirm that the D-end products control the transport of receptor to the cell surface.

Other studies were performed with 61-85 fragments of D$^k$ antigens, as well as the use of a number of control peptides. Insulin activity was segregated into two factors, tyrosine kinase activity and glucose uptake.

Peptides

The two MHC Class I derived peptides D$^k$-(61-85), and K$^k$-(61-85) are both from the same region of the α1 domain of the MHC Class I molecules (Klein, Natural history of the major histocompatibility complex (Wiley, New York)). Both peptides were synthesized by Applied Biosystems, Inc., (Foster City, Calif.), and quality controlled by mass spectrometry.

The D$^k$-(61-85), and K$^k$-(61-85) peptides were iodinated for some experiments using carrier-free Na$^{125}$I (Amersham) and iodobeads (Pierce) by incubating for 20 min., then purified by reversed-phase HPLC on a C$_{18}$ column (Beckman) in a linear 30–50% gradient of CH$_3$CN in 5 mM trifluoroacetic acid (TFA). The $^{125}$I-labeled peptide eluting first was stored at 4° C. in 50% CH$_3$CN/5 mM TFA. The labeled peptides were stable under these conditions for at least 3 months.

Control Peptides: ACTH-(1-24) (human), ACCK-33 (porcine), dynorphin A (porcine), β-endorphin-(1-27) (camel), glucagon (human), and prosomatostin-(1-32) (porcine) were all purchased from Peninsula Laboratories, Belmont, Calif. The A-chain and B-chain of insulin (porcine) and glucagon-(1-21) (human) were obtained from Novo Industry, Denmark. ACTH-(1-24) was used a routine control peptide.

Purified Insulin Receptor

The purified human IR and the cloned cytoplasmic kinase domain (IRKD) have been described (Ellis et al., (1988) *Virology* 62:1634-39; Roth et al., (1986) *J. Biol. Chem.* 261:3753-57). Briefly, the human IR was purified from placenta by immunoaffinity columns, using monoclonal antibodies and binding of IR to wheat germ agglutinin. The product was a tetramer with two heavy chains, each ~130 kDa, and two light chains, each ~90 kDa.

Tyrosine Kinase Activity

The cytoplasmic, cloned IRKD was constructed from the IR sequence (Ebena et al., (1985) Cell 40:747–758; Ullrich et al., (1985) Nature 313:756–761) and expressed in insect cells by using a baculovirus expression vector. The domain is soluble ($M_r \sim 48$ kDa) and the kinase activity is constitutively expressed in vitro. The IRKD was purified to homogeneity by immunoaffinity chromatography.

The procedures to measure kinase activity of the purified IR and IRKD, and the effects of insulin have been described elsewhere (Roth et al., (1986) supra). Briefly 5.0 µl purified IR was mixed with 5.0 µl insulin (final concentration 1.0 µM) and the buffer (50 HEPES, pH 7.6, 150 mM NaCl, 0.1% Triton X-100) added to a final volume of 20 µl. When peptide was used, it was added in 5.0 µl, the volume adjusted to 20 µl by adding buffer, and the mixture incubated (1 hr, 4° C.). After incubation, 10 µl of a solution containing 2.5 µCi $^{32}$P-labeled ATP (3,000 Ci/mmol; γ-labeled; Amersham) 50 mM HEPES, pH 7.6, 150 mM NaCl, 0.1% Triton X-100, 37.5 µM unlabeled ATP, 15 mM $MgCl_2$, and 6 mm $MnCl_2$ was added to a final volume of 30 µl. The mixture was then incubated for 30 min. at 24° C.

After incubation, 15 µl sample buffer was added, and the sample was boiled for 5 min., and run on 10% SDS-PAGE overnight. The gel was dried, and autoradiograms processed with an exposure time of 5–10 hr. For quantitative estimates the β-subunit band of IR and the IRKD bands were cut out and counted dry (Cerenkov) in a scintillation counter.

Substrate phophorylation was done with poly-([Glu,-Tyr];4:1) (Sigma) as substrate. The substrate was added to a final concentration of 1.0 mg/ml and the phosphorylation assay was conducted as described above. For quantitative estimates the entire lane from just below the insulin receptor band to a 20-kDa marker was cut out and counted or the substrate was precipitated with TCA. For the latter, 5 µl sample was dotted on to 3 MM paper (Whatman), washed 30 min. in ice cold 10% TCA, boiled 10 min. in 5% TCA, then washed twice in distilled water and twice in ethanol, and finally dried and counted.

Insulin Binding

Porcine monoiodinated [$^{125}$I]-insulin (iodinated at Tyr A14; 1,900–2,000 Ci/mmol) was obtained from NOVO Industry and Amersham. Unlabeled porcine insulin (NOVO) was dissolved in 10 mM HCl at 1 mM and stored immediately at −20° C.

The plate assay for insulin binding to its purified receptor has been described (Morgan and Roth (1985) Endocrinology 116, 1224–1226). Briefly, 50 µl of affinity-purified rabbit anti-mouse IgG (Jackson Immuno Research Lab., Inc., West Grove, Pa.) (40 µg/ml) in 20 mM $NaHCO_3$, pH 9.6, was added to 96-well polyvinyl chloride (PVC) plates. The plates were incubated (17–20 hrs, 4° C.), washed thrice in 50 mM HEPES, pH 7.8, with 150 mM NaCl, 0.1% Triton X-100, 0.05% BSA, and $2\times10^{-8}$M monoclonal antibody (Amac, Inc., Westbrook, Me.) was added. After incubation (1 hr, 24° C.), the plates were washed and insulin binding measured.

For binding measurements, $^{125}$I-insulin ($3\times10^{-10}$M) was added together with increasing amounts of unlabeled insulin, and incubated (90 min., 24° C.), washed, and the amount of free and bound $^{125}$I-labeled insulin measured. Bound insulin was determined by eluting IR off the plate with 0.1M HCl and measuring in a γ-counter. For data analysis, non-specific binding was defined as the amount bound in presence of $10^{-6}$M unlabeled insulin.

Results

The effect of $D^k$-(61–85) on both substrate (poly-[E,Y]) phosphorylation and IR autophosphorylation as a function of the peptide concentration, wherein IR tyrosine kinase activity is induced with $10^{-6}$M insulin was determined. Both are strongly inhibited at a concentration of µM $D^k$-(61–85). The basal activity of IR (no insulin added) is inhibited 24–40% by $D^k$-(61–85) and $K^k$-(61–85). The effect of $K^k$-(61–85) is significantly weaker than $D^k$-(61–85) on autophosphorylation, with $EC_{50}$ values [95% confidence intervals] of 4.0 µM [2.2–7.2 µM] and 1.2 µM [0.3–2.2 µM] for $K^k$(61–85) and $D^k$-d(61–85), respectively, whereas no difference is observed in respect to substrate phosphorylation. None of the control peptides (e.g. ACTH-(1–24) are substrates for IR tyrosine Kinase.

No significant depletion (degradation or adsorption), as examined by HPLC and $^{125}$I-labeled $D^k$-(61–85), $K^k$-(61–85), ACTH-(1–24), or dynorphin A is observed during the experimental period at concentrations above 0.1 µM. The $D^k$-(61–85) peptide does not affect IRKD phosphorylation, as demonstrated by pre-incubation of maximally autophosphorylated and $^{32}$P-labeled IR for 1 hr on ice with 10 µM peptide and subsequent incubation with 500 µM cold ATP for 0–60 min. at room temperature.

The $D^k$-(61–85) has no effect on the binding of insulin to IR based on affinity. The $EC_{50}$ IR autophosphorylation is about $3\times10^{-9}$M insulin, corresponding approximately to $K_d(2.8\times10^{-9}$M). $D^k$-(61–85), at 10 µM inhibits autophosphorylation at all insulin concentrations.

$D^k$-(61–85), 3 µM inhibits the insulin-induced IR autophosphorylation, but not the insulin receptor kinase domain phosphorylation, when IR and IRKD are used at comparable activities. IR is not a significant substrate for IRKD in the absence of insulin. IR becomes a significant substrate for IRKD when insulin is added. This observation is facilitated by the inhibitory effect of the peptide on IR autophosphorylation, because the IR phosphorylation as mediated by the tyrosine kinase of IR itself and the phosphorylation mediated by IRKD would otherwise be indistinguishable.

In the next study, the uptake of glucose in rat adipocytes was performed. Adipocytes are prepared from non-starved male rat epididymal fat pads (1.2–1.6 g fat per rat) by collagenase digestion. The buffer is KRH with 5% BSA: only plastic tubes are used. The digest is filtered (25µ) washed and resuspended in approximately 4×the cell volume (estimated by lipocrit). An aliquot is removed for Coulter counting after staining with 2% osmium tetroxide, filtration and dilution in saline. 50 µl of adipocyte suspension is added to the pre-incubation mix; 300 µl buffer, 50 µl insulin (80 nM) or buffer; 50 µl test solution (10×) or buffer and incubated for 30 min. at 37° C. in a shaking water bath. A blank without cells is included for background counting. D-[$^{14}$C]-glucose is subsequently added (about $10^5$ dpm/sample) and incubation continued for 60 min. The incubation is terminated by layering the 400 µl sample on top of silicone oil, followed by a 30 sec. microfuge spin, and cutting the adipocytes (thin layer of cells on top of the oil, buffer under oil) into LS vials with scintillation fluid. Glucose concentration was about 300 nM (sp.a.295 mCi/mmol).

The effect of increasing concentrations of insulin in 30 μM D$^k$-(61–85) on glucose uptake was determined. Insulin induced maximally an 8–11 fold increase in glucose uptake as compared to basal uptake. Addition of D$^k$-(61–85) increased the maximal uptake to about 14–18 fold of basal, a glucose uptake above maximal insulin stimulation. At low concentrations of insulin (plasma level and lower), 30 μM D$^k$-( 61–85) increased glucose uptake as much or more than insulin on a molar basis.

The maximal effect of D$^k$-(61–85) was obtained at 15 μM. It is found that the increase varies with the particular peptide batch, where the insulin effect of the peptide may vary from about 20% to 100%.

Various fragments of D$^k$-(61–85) were prepared by enzymatic digestion with specific peptidases: endo K, which gave fragments 60–68 and 69–85; endo E, which gave fragment 78–85; CP Y, which provided fragment 61–84; and in addition, the starting fragment was iodinated, which would be expected to occur at the terminal tyrosines. Each of the fragments were tested for biological activity after purification (greater than 95%) by HPLC and added to cells to a final concentration of 30 μM. The results reported as percent activity of the mean ±SE, with the starting fragment being 100 are as follows (61–68) 19±22; (69–85) 87±2; (78–85) 15±3; (61–84) 19±3; iodinated fragment 9±10.

The effect of D$^k$-(61–85) in whole rats was determined. D$^k$-(61–85) (2.5 mg/kg) and insulin (10 μg/kg) on the blood glucose levels in rats (100–300 g) was determined. The peptide and insulin were injected i.v. after the animals had been anesthetized with pentobarbital. All animals were starved 16–20 hrs. prior to experimentation. Each determination was based on results as obtained from 42 rats, where the same rats were used in the four treatment schedules. The schedules were a control, a peptide by itself, insulin by itself, and insulin plus peptide. The control showed no significant change in blood glucose over the 240 min. during which determinations were made. The peptide, at about 20 min., the blood glucose had dropped to about 65% of its original value and then slowly rose back to about the original value at about 90 min. and was maintained about the same level. A similar result was observed with the injection of insulin. However, where the insulin and peptide were injected together, the glucose dropped within about 20 min. to about 55% of its original value and slowly rose to about 85% of its original value at about 195 min. then gradually increased to about 90% at about 240 min. Calculation of the area between the control curve and the experimental curves from T=0 to T=240 showed that the area for insulin plus peptide is significantly larger than that of insulin or peptide alone, indicating a prolonged hypoglycemia period as compared to the insulin or peptide alone.

In order to determine the main target organs for peptide mediated glucose uptake, the glucose uptake in various organs was analyzed as a function of oligopeptide injection i.v. The main target organs for peptide mediated glucose uptake are skeletal muscle, liver and kidney, when the size of the organ is considered. It is notable that some of these organs are not affected by insulin injection. The procedure employed was the injection of $^{14}$C-2-deoxyglucose 60 min. after injection of insulin plus peptide and the organ content of $^{14}$C measured 30 min. later, i.e. 90 min. after injection of peptide.

Based on the above data, it may be concluded that D$^k$-(61–85) peptide enhances cellular glucose uptake both in the absence and presence of insulin. Peptide effect is increased upon stimulation with insulin. Maximal peptide effect is reached at a peptide concentration of 10–20 μM. The peptide causes enhanced glucose uptake significantly above that induced by maximal insulin stimulation. The effect in vitro is maximal after 20 min. incubation of the cells with peptide. Intravenous injection of 2.5 mg/kg D$^k$-(61–85) peptide causes a decrease in blood glucose in whole animals. It is accentuated when insulin is injected together with the peptide. Glucose uptake as induced by peptide is particularly pronounced in muscle, liver and kidney, but the peptide does not result in increased levels of serum-insulin.

EGFR Study

Peptides—Peptides (Table 6) were synthesized by Applied Biosystems, Inc. (Foster City, Calif.). The crude D$^k$-(61–85) peptide was purified by preparative high performance liquid chromatography (HPLC) to better than 97% homogeneity as judged by analytical HPLC monitoring of absorbance at 214 and 278 nm. The β2- and α3-derived peptides were more than 90% pure. Identity was confirmed by amino acid composition and mass spectrometry. The peptides were dissolved in 0.1M HCl and stored at 1.0 mM in 200 μl aliquots at −80° C.

TABLE 6

| MHC Class I Derived Peptides | |
|---|---|
| Peptide | Sequence* |
| D$^k$-(61–85) | ERETQIAKGNEQSFRVDLRTLLRYY (SEQ ID NO: 14) |
| D$^b$-(137–161) | DMAAQITRRKWEQSGAAEHYKAYLE (SEQ ID NO: 15) |
| D$^b$-(152–176) | AAEHYKAYLEGECVEWLHRYLKNGN (SEQ ID NO: 16) |
| D$^b$-(197–221) | GEVTLRCWALGFYPADITLTWQLNG (SEQ ID NO: 17) |

*Single-letter amino acid code is used.

Hormones—EGF (mouse) and PDGF (human) were purchased from Collaborative Research, Inc., Bedford, Mass. TGF$_\alpha$ (rat) was purchased from Peninsula Laboratories, Belmont, Calif. $^{125}$I-labeled EGF (480 Ci/mmol) was purchased from ICN Biomedicals, Inc.

Preparation of Adipocytes—The procedure has been described in detail previously. Briefly, male Wistar rats (100–150 g) were decapitated, and the epididymal fat pads removed and minced with scissors into KRHB (Krebs-Ringer/HEPES/Bovine serum albumin (BSA) buffer: 80 mM NaCl, 4.7 mM KCl, 2.5 mM CaCl$_2$, 1.2 mM MgSO$_4$, 50 mM HEPES, 5% BSA (Sigma, radioimmunoassay grade), pH 7.2) containing 5 mM D-glucose and 1 mg/ml collagenase (type I, Worthington) and digested (1 hr, 37° C.) with gentle shaking (250 cycles per minute). The adipocytes were washed five times in KRHB (each wash in a volume ten times the cell volume). The adipocyte layer was finally diluted with KRHB to a 10% (v/v) suspension as estimated by the volume of packed cells (lipocrit).

Glucose uptake in vitro—The uptake of [$^{14}$C]glucose (D-[U-$^{14}$C]glucose, Amersham, (300 Ci/mol)) by isolated rat adipocytes was measured as follows unless otherwise stated: 50 μl adipocyte cell suspension was pipetted into "Nunc-Immuno tube minisorp" (Nunc, Denmark) and preincubated at 37° C. with gentle shaking (225 cycles per minute) for 30 min. Hormones and peptides were added in 50 μl KRHB and incubated for 30 min at 37° C. Before addition to cells, all solutions were neutralized to pH 7.2. [$^{14}$C]glucose tracer (~100,000 dpm) was added and the incubation continued for another 20 minutes at 37° C. The assay was terminated by centrifugation of 100 μl sample on top of 250 μl silicone oil (Thomas Scientific) in 500 μl tubes in a microfuge (10,000×g) for 1 min. The tube was cut just below the adipocyte layer and the amount of radioactivity in the adipocytes determined by scintillation counting. The precise concentration of [$^{14}$C]glucose was calculated from total counts added. Data were not corrected for trapping, which in previous experiments was found to be negligible.

Cell-associated $^{125}$I-labeled EGF—50 μl adipocyte cell suspension was pipetted into "Nunc-Immuno tube minisorp" (Nunc, Denmark) and preincubated at 37° C. with gentle shaking (225 cycles per minute) for 30 min. The cells were incubated for 30 minutes at 37° C. with 50 μl KRHB containing 600 pM $^{125}$I-labeled EGF and different concentrations of non-radioactive EGF. The assay was terminated by centrifugation of 75 μl sample as described above for glucose uptake, and the cell-associated as well as the free $^{125}$I-labeled EGF was determined by γ-counting. Non-specific cell-associated $^{125}$I-labeled EGF was defined as cell-associated $^{125}$I-labeled EGF in the presence of 128 nM non-radioactive EGF. The data were calculated as specific cell-associated $^{125}$I-labeled EGF and the maximal value was in each experiment set to 100%.

Results

EGF alone stimulated glucose uptake in rat adipocytes ~50% above basal. However, when $D^k$-(61–85) peptide was added at a concentration of 30 μM, the glucose uptake was enhanced to 5–6 fold above basal uptake. The peptide did not affect the $EC_{50}$ for the EGF effect on glucose uptake. Maximal effect of EGF and $D^k$-(61–85) was obtained after approximately 10–20 min. The peptide was active in a concentration range of 5–30 μM and had an $EC_{50}$ ~10–15 μM. The maximal effect obtained with EGF and peptide alone was ~50% of maximal effect obtained with insulin. EGF and peptide in combination with increasing concentrations of insulin resulted in increasing glucose uptake until the maximal level attained with insulin and peptide was reached.

Experiments with $^{125}$I-labeled EGF demonstrated specific cell-associated EGF with an apparent affinity in the low nanomolar range, which corresponds to the affinity for EGF binding reported with adipocytes and other cell types. The presence of the peptide did not affect the amount of specific cell-associated $^{125}$I-labeled EGF. The total cell-associated $^{125}$I-labeled EGF was 119±12 (mean ±S.E.M.; n=3) in the presence of peptide (no peptide=100) and there was no difference in non-specific cell-associated $^{125}$I-labeled EGF (57±8 with peptide versus 53±12 without peptide).

Incubation of adipocytes with 50 nM $TGF_\alpha$ increased [$^{14}$C]glucose uptake ~50% above basal, whereas 50 nM $TGF_\alpha$ in combination with 30 μM $D^k$-(61–85) increased [$^{14}$C]glucose uptake ~5 fold above basal. This effect of $TGF_\alpha$ alone or in combination with $D^k$-(61–85) on [$^{14}$C]glucose uptake is thus similar to the effect found for EGF.

Platelet derived growth factor (PDGF) alone or together with $D^k$-(61–85) had no effect on glucose uptake in adipocytes.

Three other peptides derived from the MHC class I molecule were also tested for their effect on glucose uptake when combined with EGF. $D^b$-(137–161) and $D^b$-(152–176), derived from the β2 region, and $D^b$-(197–221), derived from the α3 region, had no or only a small effect on glucose uptake compared to the $D^k$-(61–85) peptide.

It is evident from the above results that surface membrane receptors involving transduction of signals, as exemplified by the insulin and EGF receptors, are modulated by MHC Class I antigens, particularly H-2D and -L of mice and HLA-B and -C of humans. A wide variety of physiological processes, both in vitro and in vivo, may be regulated by controlling the interaction between the appropriate Class I antigen and the surface membrane receptor, by a variety of techniques which allow for the enhancement or reduction of the interaction between the Class I antigen and the surface membrane receptor.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

What is claimed is:

1. A method for modulating the response of the insulin receptor to a ligand comprising contacting, for a time and under conditions sufficient for binding, a mammalian cell comprising an insulin receptor on its cell surface with an effective amount of an oligopeptide consisting of at least eight amino acid residues of the MHC class I derived sequence NH$_2$-W E R E/I T Q I A K G N/Q E Q S/W F R V D/N L R T L L R Y Y—COOH, wherein said oligopeptide comprises at least the amino acid residues L R T L L R Y.

2. The method of claim 1, wherein said modulation consists of a potentiation of the effects of insulin on blood glucose levels.

* * * * *